United States Patent [19]

Schlensker

[11] Patent Number: 4,829,778
[45] Date of Patent: May 16, 1989

[54] MEASURING GAS COOLING DEVICE

[75] Inventor: Herbert Schlensker, Leverkusen, Fed. Rep. of Germany

[73] Assignee: VIA GmbH, Fed. Rep. of Germany

[21] Appl. No.: 140,830

[22] Filed: Jan. 5, 1988

[30] Foreign Application Priority Data

Sep. 23, 1987 [DE] Fed. Rep. of Germany ... 8712814[U]

[51] Int. Cl.[4] ............................................. F25D 21/00
[52] U.S. Cl. .......................................... 62/272; 62/93
[58] Field of Search .................... 62/93, 150, 272, 283

[56] References Cited

U.S. PATENT DOCUMENTS

| 2,218,594 | 10/1940 | White . |
| 2,681,797 | 6/1954 | Van Vliet . |
| 3,696,636 | 10/1972 | Mille . |
| 3,861,165 | 1/1975 | Hirano ...................................... 62/93 |
| 3,871,444 | 3/1975 | Houser et al. . |
| 4,147,500 | 4/1979 | Karlsoen . |

FOREIGN PATENT DOCUMENTS

| 3117431 | 3/1982 | Fed. Rep. of Germany . |
| 3111415 | 10/1982 | Fed. Rep. of Germany . |
| 2155770 | 5/1973 | France . |
| 598084 | 2/1948 | United Kingdom . |

Primary Examiner—Henry A. Bennet
Attorney, Agent, or Firm—Lerner, David, Littenberg, Krumholz & Mentlik

[57] ABSTRACT

A heat exchanger for a cooling device for the removal of water vapor from measuring gases that provides for the separate circulation of the measuring gas and the refrigerant between which heat exchange contact is maintained by a liquid heat transfer medium.

12 Claims, 3 Drawing Sheets

MEASURING GAS COOLING DEVICE

FIELD OF THE INVENTION

The present invention relates to cooling devices for the removal of water vapor from measuring gases, and more particularly relates to cooling units comprising heat exchangers that provide for the separate circulation of the measuring gas and the refrigerant and the condensation of and removal of water vapor from the measuring gas by a condensation separator.

BACKGROUND OF THE INVENTION

Analytical devices utilizing measuring gases are known in the art as useful for the measurement of process gases and combustion products. For certain analytical measurements it is desirable to maintain a constant dew point for the measuring gas to accurately calibrate the analytical device and to eliminate the effect of water vapor on the analytical measurement results. Measuring gas analytical devices capable of maintaining a constant dew point for the measuring of gases usually comprise a means for the condensation and removal of water vapor from the measuring gas. This water vapor condensation and removal means typically comprises a heat exchanger for the cooling of the measuring gas and condensation of the water vapor, that also has a condensation separator for removal of the condensed water vapor from the measuring gas.

A typical heat exchanger and condensation separator for the removal of water vapor from a measuring gas is disclosed in German Pat. No. 31 11 415 A1. The heat exchanger of this device essentially consists of a pipeline for transporting the measuring gas wrapped around a collector for the cooled gas from which the water vapor condensate precipitates, which is immersed in a sealed refrigerant bath. This design has several drawbacks. Typical refrigerants attack most synthetic plastic materials; therefore, the choice is limited for the parts of the device, most of which are in contact with the refrigerant, especially the measuring gas line, which is immersed in the refrigerant, and the heat exchanger housing, which holds the refrigerant.

An additional problem is presented in the selection of materials for the measuring gas line because the materials for this line must also be acid resistant. Additionally, in many applications, the refrigerant is supplied at a higher pressure than the measuring gas, e.g., between about 2 to 3 bars versus between about 0.1 to 0.5 bars, and accordingly, the other parts of the device are also limited to materials capable of withstanding the higher refrigerant pressures. Consequently, measuring gas cooling devices have in the past been limited to being manufactured from materials such as specialty steels, which are undesirable because they are expensive, and glass, which is undesirable because it is fragile.

Cooling devices for the removal of water vapor from measuring gases are desired that can be manufactured from durable, inexpensive materials which resist attack from substances to which they are exposed. Therefore, it is an object of the invention to provide a measuring gas cooling device with reduced production costs by manufacturing the heat exchanger for the device with parts made from durable, inexpensive materials.

It is a further object of the invention to provide a measuring gas cooling device heat exchanger with parts made from durable, inexpensive materials by containing the refrigerant in a refrigerant line so that the other parts of the device need not be resistant to attack from the refrigerant or withstand the refrigerant pressure.

It is an object of the invention to provide a measuring gas cooling device in which the measuring gas line and heat exchanger housing, or container, are made from durable, inexpensive materials by containing the refrigerant in a refrigerant line so that the measuring gas line need be resistant to attack only from the measuring gas and, along with the heat exchanger container, need not be resistant to attack from the refrigerant or withstand refrigerant pressures, if higher.

It is an object of the invention to provide a measuring gas cooling device heat exchanger with a container that is transparent to permit monitoring of the interior of the device for maintenance and other purposes by containing the refrigerant in a line that permits the refrigerant container to be manufactured from durable, transparent material that need not withstand refrigerant pressure or attack.

The listing of objectives provided herein or of features of the inventions is not intended to be exhaustive but merely illustrative.

Other objects will become apparent to one of average skill in the art in the further description of the invention.

SUMMARY OF THE INVENTION

According to the present invention, it has been found that the heat exchanger refrigerant for a measuring gas cooling device heat exchanger can be enclosed in a refrigerant line without detracting from the heat transfer function of the refrigerant by enclosing both the refrigerant line and a measuring gas line in a sealed container filled with a heat transfer liquid. The invention comprises separating the refrigerant from the measuring gas line in this manner and using materials for the measuring gas line and other parts of the cooling device that then need not be capable of withstanding attack from or the pressure of the refrigerant. This increases the range of low-cost, durable materials from which these components can be made.

According to the present invention, a heat exchanger for the cooling of a measuring gas for the removal of water vapor comprises a container having a top and a bottom filled with a heat transfer liquid and having a condensation separator comprising a pipe section with two ends disposed vertically in the container. One end of the condensation separator passes sealingly through the top of the container, an the other end of the condensation separator passes sealingly through the bottom of the container. The measuring gas can pass upwardly through the condensation separator, and condensate forming therein can pass downwardly through the end of the condensation separator at the bottom of the container. In accordance with invention, aqueous solutions of sodium chloride or a glycol can be used as the heat transfer liquid. The heat exchanger also comprises a measuring gas pipeline, one end of which is connected proximately to the bottom of the container, within the container. The measuring gas pipeline is in heat exchange contact with the heat transfer liquid and passes sealingly through the top wall of the container. In accordance with the invention, the measuring gas line is made from an acid resistant material such as polyvinylidene fluoride. The measuring gas can pass into the measuring gas pipeline at the top of the container, be cooled by the heat transfer liquid, and pass into the end of the condensation separator proximate to the bottom of the container.

The heat exchanger further comprises a refrigerant pipeline, both ends of which pass sealingly through the top wall of the container. The refrigerant pipeline is in heat exchange contact with the heat transfer liquid, and refrigerant can pass through the refrigerant pipeline and cool the heat transfer liquid. In accordance with the invention, the refrigerant liquid R12 can be used as the refrigerant.

In one aspect of the invention, the measuring gas line is spirally disposed in a downward direction around the condensation separator. In another aspect of the invention, the refrigerant line is spirally disposed around the condensation separator. In a further aspect of the invention, the spirally disposed measuring gas line defines an annular space between the measuring gas line and the condensation separator, and the refrigerant line is spirally disposed within this annular space, around the condensation separator. In one embodiment, the refrigerant line that is spirally disposed within the annular space defined around the condensation separator by the measuring gas line comprises a first inner spiral section coaxial to a second outer spiral section with both spiral sections connecting at their lower ends and one spiral section connecting at its upper end to the refrigerant inlet and the other spiral section connecting at its upper end to the refrigerant outlet. In another embodiment, the inner spiral is connected to the refrigerant inlet.

In one embodiment, the container has a sealable opening for adding the heat transfer liquid. In another embodiment, the container is permanently sealed.

The parts of the heat exchanger not in contact with the measuring gas or refrigerant, such as the container, can be made from polyvinylchloride. In one embodiment, the container is made from transparent polyvinylchloride to permit inspection of the interior parts.

DETAILED DESCRIPTION OF THE PREFERRED EMBODIMENT

Figure 1:
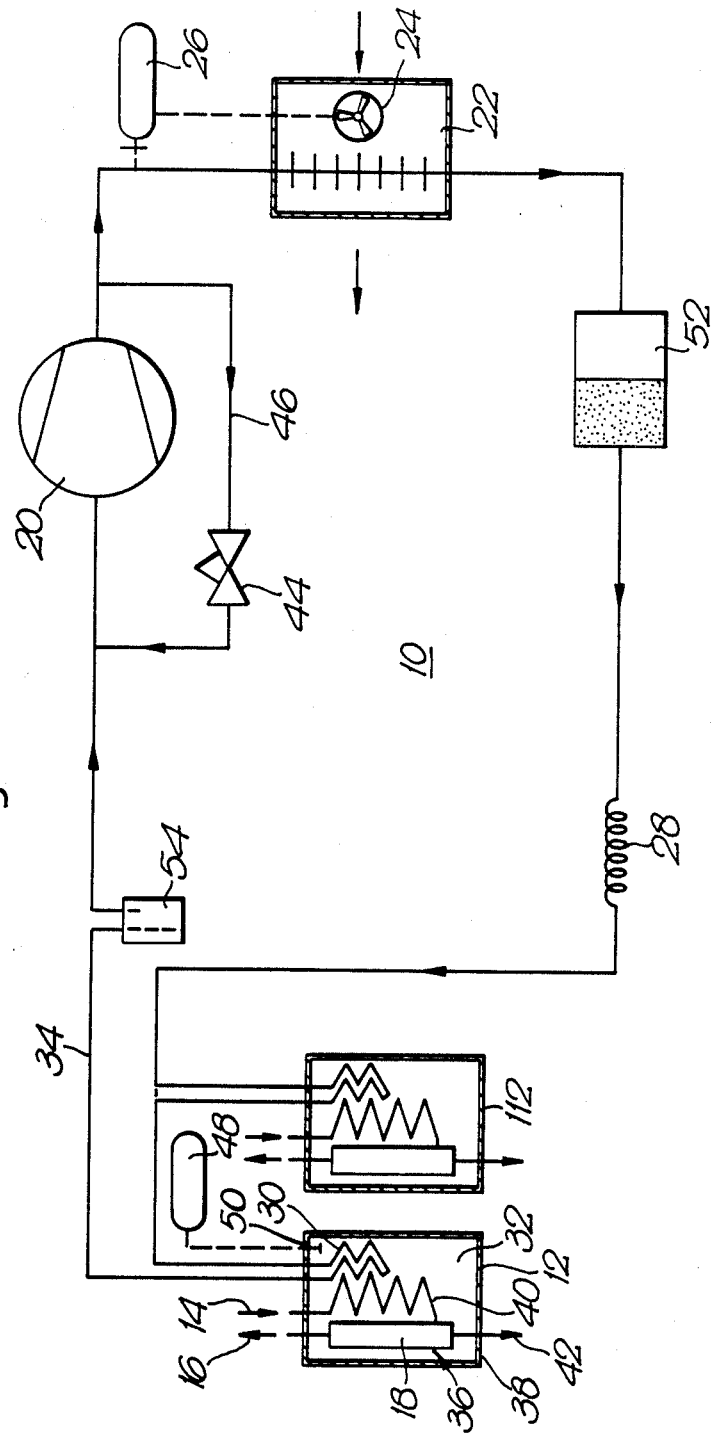
FIG. 1 is a schematic view of the construction of a measuring gas cooling device with the features according to the preferred embodiment of the invention.

As stated above, it has been found that the refrigerant for a measuring gas cooling device heat exchanger can be enclosed in a transporting line without detracting from the heat transfer function of the refrigerant. The measuring gas and refrigerant lines are enclosed in a sealed container filled with a heat transfer liquid to facilitate heat transfer between the two. The lines are preferably in the form of pipes coiled around a condensation collector tube of larger diameter, with the measuring gas line coiled externally around the collector tube with the end connected to the base of the collector tube to permit the entry into the collector tube of cooled measuring gas from which water vapor has condensed. It is in this collector tube that condensed water vapor precipitates and the measuring gas is drawn off for analysis. Most preferably, the measuring gas line coils around the collector tube in a manner that defines an annular space between the collector tube and measuring gas line within which the refrigerant line is coiled around the collector tube.

In accordance with the invention, the heat exchanger also comprises a means for the circulation and cooling of the refrigerant, and both ends of the refrigerant line pass tightly through the top wall of the heat insulated container and connect with this circulation means. In a preferred embodiment of the invention, the refrigerant line is spirally disposed within the annular space defined around the collector tube of the condensation separator by the measuring gas line and comprises a first inner spiral section defined around the collector tube and a second outer spiral section, with one spiral section connected to the coolant circulation inlet of the other spiral section connected to the coolant circulation outlet. Preferably, the first inner spiral section is connected to the coolant inlet.

In accordance with the invention, the heat exchanger also comprises a means for the introduction and drawing off of the measuring gas and a means for removal of the collected water vapor condensate.

The refrigerant used for the heat exchanger is preferably the refrigerant liquid R12. The refrigerant line is preferably metal because most plastics are not resistant to attack from typical refrigerants. Most preferably, the metal used for the refrigerant line is copper. The other parts of the heat exchanger need not be resistant to coolant attack and are preferably made from plastic, most preferably polyvinylchloride. The measuring gas line, however, must be acid resistant. It is also preferably made from low-cost, durable plastic; this material is most preferably polyvinylidene fluoride.

In accordance with the invention, the preferred embodiment is described as follows:

The measuring gas cooling device comprises one or more heat exchangers (12,112) into which is introduced measuring gas (14) drawn, for example, from an exhaust channel, and in some situations, exhibiting variations in humidity with time. In the heat exchanger, the measuring gas is cooled to 2° C. and then released at a pipeline (16), which transports the cooled measuring gas with the water vapor removed to the measurement devices. The measuring gas condensation that occurs is condensed in a condensation separator (18). R12 is used as the refrigerant liquid. A compressor (20) condenses, to about 7 bars, the coolant, leaving the heat exchanger (12), which passes over a steam dome in accordance with the required operating conditions. The compressor comprises a pressure casing having a piston compressor driven by means of an electric motor.

In the condenser (22), the coolant is liquified, and heat is removed through a ventilator (24), which, at low ambient temperatures, can be switched off by means of a switch controlled by coolant pressure. There then follows a reduction in the pressure of the coolant from about 7 bars to about 2 bars by means of a capillary tube (28). The pressure reduced coolant is then injected into a heat exchanger pipe coil or evaporator (30), where it absorbs heat energy from the measuring gas indirectly by way of the heat transfer liquid (32) and thereby evaporates. The compressor (20) then draws the evaporating coolant back by way of the outlet refrigerant line (34). The evaporator (30), along with the heat exchanger unit (36) through which the measuring gas flows, are located in a container (38) filled with cooling brine. The heat exchanger unit (36) itself comprises a spirally wound pipe (40) with a separation container (18) and condensation drainage pipe (42) attached to it.

The measuring gas is cooled by giving off heat to the heat transfer liquid, which is cooled by the refrigerant. All three systems—the measuring gas, the heat transfer liquid, and the refrigerant—are hermetically sealed off from one another. The measuring gas exit temperature is preferably controlled by means of a hot gas bypass regulation valve (44), which draws off more or less of the refrigerant from the output of the compressor (20), depending on the refrigerant pressure at the evaporator output, and introduces it back into the compressor input via a bypass (46).

Because pressure and temperature are directly related, this hot gas bypass regulation valve guarantees, in the known manner, a constant measuring gas temperature within the measuring gas throughput area provided in the device at a set evaporator pressure, in this example 2.2 bars.

To regulate the temperature of the heat transfer liquid (32), there is a microprocessor-controlled operating control device, whereby the temperature can be determined by a sensor device (50) immersed in the heat transfer liquid.

A coolant drier (52) is also included in the coolant circuit.

If the measuring gas cooling device has more than one heat exchanger (12) for a second measuring gas path, the coolant circulation can be directed in such a way that the heat exchangers are coupled in parallel or in series.

The resulting condensate is collected by way of an external condensate container or is pumped off by means of an automatic condensate separation device.

Figure 2:
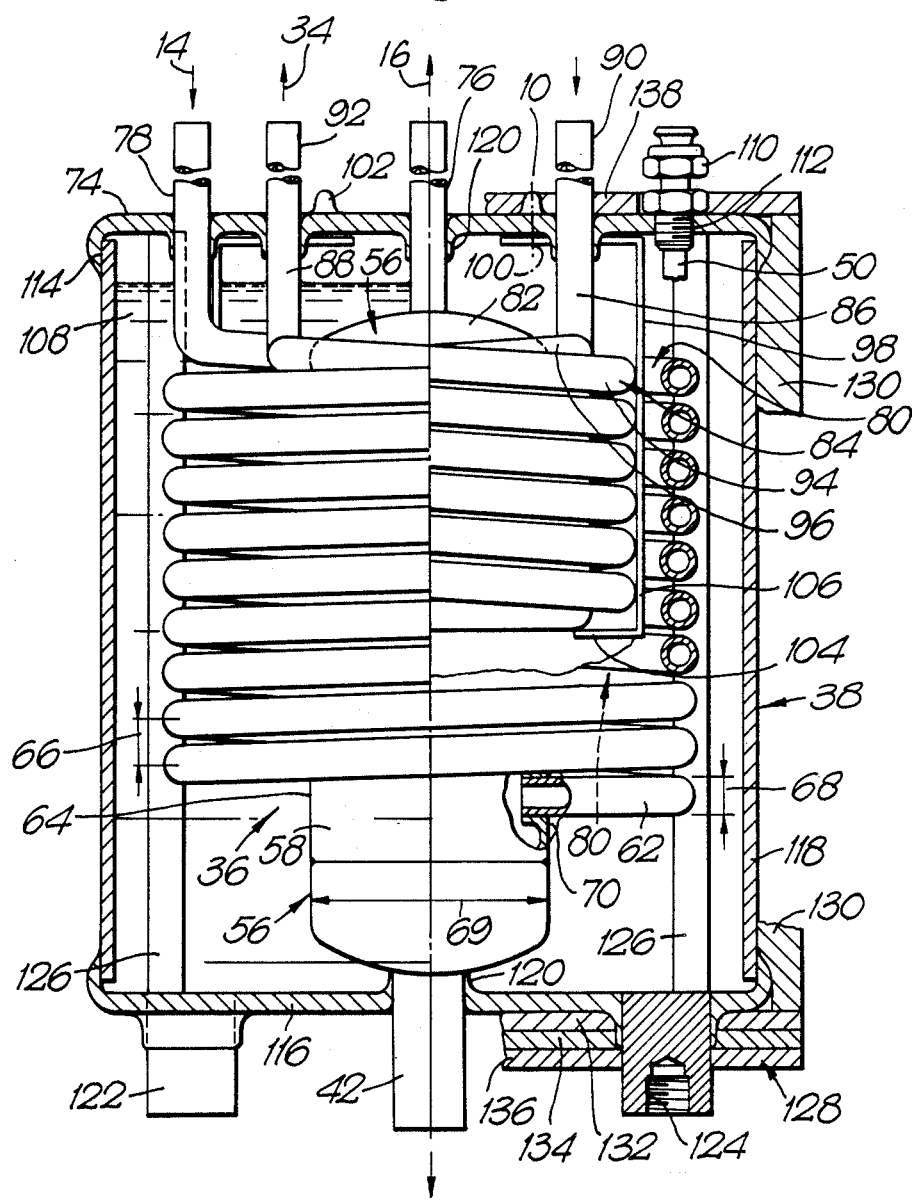
FIG. 2 is an axial section, with some of the pipe connections shown in a displaced manner, of a heat insulated container with heat exchanger and condensation separator according to the features of the preferred embodiment of the invention.

FIG. 2 shows an axial, partially displaced cross-section of a heat exchanger (12) with a heat exchanger unit (36), formed by a condensation separator pipe (56) disposed essentially vertically in a container (38), the lower end (58) of which is connected to a measuring gas pipe (62) having a pipe diameter (68) less than the diameter (69) of the condensation separator pipe (see reference number 70). The measuring gas pipe is wound upwards in a spiral (66) around the external circumference (64) of the condensation separator pipe, the upper end (82) of which and the upper end of the measuring gas pipe spiral both pass tightly through the cover-forming wall (74) of the container in the form of pipe connections (76, 78).

In contrast to the prior art in which the measuring gas pipe is wound directly on the external circumference wall of the condensation separator pipe, in the present invention, an annular space is left between the measuring gas pipe spiral and the external surface of the condensation separator pipe so that the refrigerant pipe (84) can be arranged in a spiral around the condensation separator pipe, the two of ends of which (86, 88) pass tightly through the cover-forming wall of the container in the form of pipe connections (90, 92) for the introduction and removal of coolant.

The refrigerant pipe spiral forms a first external spiral section (94) and a second, coaxial, inner spiral section (96) which are connected to each other at their lower ends and are connected at their upper ends to the refrigerant outlet and the refrigerant inlet. In particular, the upper end of the inner spiral is connected with the refrigerant inlet. The external spiral and refrigerant outlet can be made of one section of pipe material.

The refrigerant pipe is made of metal, more especially copper, as polyvinylchloride or polyvinylidene fluoride are not refrigerant resistant. Due to its flexibility, it is desirable to surround the refrigerant pipe containing the refrigerant with supports (98). The supports comprise in this example three brackets arranged at intervals of 120°, which can be fixed by means of screws (100) to the cover, with the noses (102) forming a sealed screw thread of adequate length. The brackets support at their lower end through projection (104) the lowest spirals of the refrigerant pipe and through their lateral projection (106) support the coaxial orientation of this pipe. The support could, however, also be a cylinder with a closed wall surface, this allowing the flow of the heat transfer liquid in the container if circulation of the heat transfer liquid by pump devices is provided.

A sealed inlet, which is not shown in more detail in the figures, can be used to introduce the heat transfer liquid, or the heat transfer liquid can be added during the manufacturing process and sealed in by placing the cover on the container and sealing it at this point (114), especially if the container wall and cover are made of synthetic material. In the same way a base section (116) can be attached to the cylindrical container wall (118). For the pressure-tight passing and sealing of the individual pipe connections and the condensate drainage pipe (42) through the base wall, highly drawn areas (12) are provided that have a longer area of contact with the connections and are thus tighter. In the same way, fastening elements (122) are fixed to the container base. These have fastening thread holes (124). For recording the heat transfer liquid temperature, the aforesaid sensor can be introduced into the container through a corresponding opening (112) in the cover.

Appropriate supports (126) can be used to support the measuring gas pipe, which extend from the base plate to the cover and are provided at intervals of 120°.

The container is surrounded by heat insulation (128), formed from cylinder-shaped or plate-shaped rigid plastic sections (130, 132, 134, 136, and 138).

Figure 3:
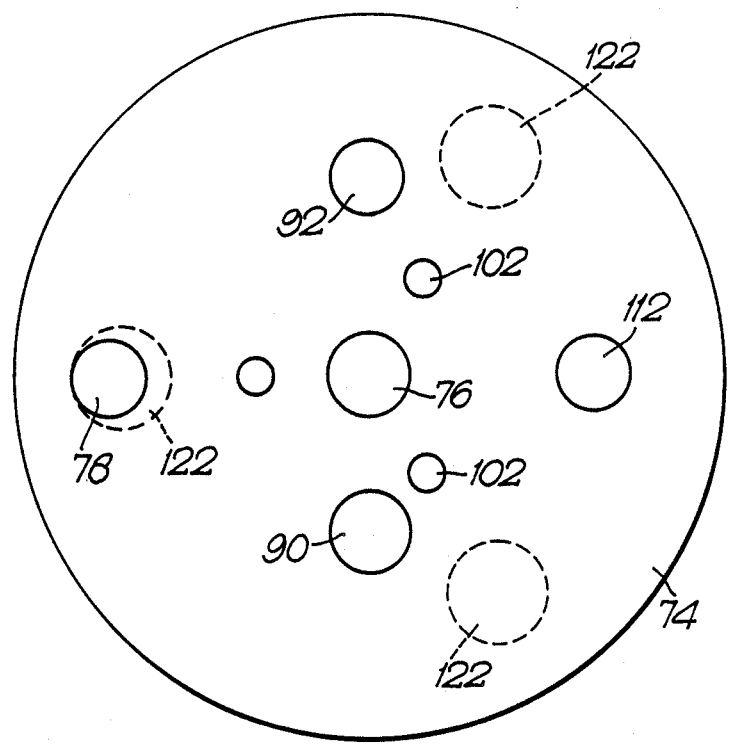
FIG. 3 is a view from above depicting the various pipe connections and the cover of the container in FIG. 2.

FIG. 3 shows a view from above onto the container, particularly the cover, with connection pipes for the measuring gas and refrigerant (shown displaced in FIG. 2). The sensor opening (112) can also be seen, as can feet (122) and noses (102). The feet shown on the right-hand side of FIG. 3 and the noses oriented thereto are also shown displaced in FIG. 2.

The foregoing description and examples should be understood by way of illustration rather than by a limitation of the present invention as defined in the claims. As will be appreciated, numerous variations and combinations of the features set forth in the foregoing description and examples can be utilized without departing from the present invention.

I claim:

1. A heat exchanger for the cooling of a measuring gas and for the removal of water vapor therefrom, comprising:
    a container filled with a heat transfer liquid, said container including a top and a bottom,
    a condensation separator comprising a pipe section disposed vertically in said container, said condensation separator including a first end and a second end, said first end of said condensation separator passing sealingly through said top wall of said container and said second end of said condensation separator passing sealingly through said bottom wall of said container, whereby a measuring gas can pass upwardly through said condensation separator and condensate forming therein can pass downwardly through said second end of said condensation separator, a measuring gas pipeline having a first end and a second end, said first end of said measuring gas pipeline being connected proximately to said second end of said condensation separator, within the bottom wall of said container, and being spirally disposed around said condensation separator thereby defining an annular space between said measuring gas line and said condensation separator, said measuring gas line being in heat exchange contact with said heat transfer liquid and passing sealingly through said top wall of said container, whereby said measuring gas can pass into said second end of said measuring gas pipeline, be cooled by said heat transfer liquid, and pass into said condensation separator, and a refrigerant pipeline having a first end and a second end, both said first and second ends of said refrigerant pipelines passing sealingly through said top wall of said container, said refrigerant pipeline being spirally disposed within said annular space, around said condensation separator and the portion of said refrigerant pipeline between said first and second ends being in heat exchange contact with said heat transfer liquid, whereby a refrigerant can pass through said refrigerant pipeline and cool said heat transfer liquid within said container.

2. The heat exchanger of claim 1, wherein the refrigerant line comprises a first inner spiral section and a second coaxial outer spiral section, both of said spiral sections connected together at their lower ends, one of said spiral sections being connected to a refrigerant inlet and the other of said spiral sections being connected to a refrigerant outlet.

3. The heat exchanger of claim 2, wherein said one of said spiral sections comprises said first inner spiral section.

4. The heat exchanger of claim 2, wherein said other of said spiral sections comprises said second outer spiral section and includes support means for said second outer spiral section selected from the group consisting of a cylindrical wall and a plurality of holding brackets.

5. The heat exchanger of claim 1, wherein said container includes a sealable opening for introducing said heat transfer liquid.

6. The heat exchanger of claim 1, wherein said container is permanently sealed.

7. The heat exchanger of claim 1, wherein said heat transfer liquid is an aqueous solution of a compound selected from the group consisting of sodium chloride and a glycol.

8. The heat exchanger of claim 1, wherein said measuring gas line comprises an acid resistant material.

9. The heat exchanger of claim 8, wherein said acid resistant material comprises polyvinylidene fluoride.

10. The heat exchanger of claim 1, wherein said container comprises polyvinylchloride.

11. The heat exchanger of claim 10, wherein said polyvinylchloride container is transparent.

12. The heat exchanger of claim 1 including a temperature sensor immersed in said heat transfer liquid.

* * * * *